(12) United States Patent
Wang et al.

(10) Patent No.: US 10,709,792 B1
(45) Date of Patent: Jul. 14, 2020

(54) PASSIVATED MAGNETIC NANOPARTICLES FOR CELL TARGETING AND METHODS OF PREPARATION AND USE

(71) Applicant: Verily Life Sciences LLC, South San Francisco, CA (US)

(72) Inventors: Zhan Wang, San Jose, CA (US); Nicole Peck, Redwood City, CA (US)

(73) Assignee: VERILY LIFE SCIENCES LLC, South San Francisco, CA (US)

(*) Notice: Subject to any disclaimer, the term of this patent is extended or adjusted under 35 U.S.C. 154(b) by 0 days.

(21) Appl. No.: 16/376,160

(22) Filed: Apr. 5, 2019

Related U.S. Application Data

(60) Provisional application No. 62/653,690, filed on Apr. 6, 2018.

(51) Int. Cl.
*A61K 47/60* (2017.01)
*A61K 47/69* (2017.01)
*A61K 47/68* (2017.01)
*A61K 47/54* (2017.01)
*B82Y 5/00* (2011.01)

(52) U.S. Cl.
CPC ............ *A61K 47/60* (2017.08); *A61K 47/542* (2017.08); *A61K 47/6835* (2017.08); *A61K 47/6929* (2017.08); *B82Y 5/00* (2013.01)

(58) Field of Classification Search
CPC .. A61K 47/60; A61K 47/6929; A61K 47/542; A62K 47/6835; B82Y 5/00
See application file for complete search history.

(56) References Cited

U.S. PATENT DOCUMENTS

2016/0363587 A1   12/2016   Kannan et al.
2019/0060484 A1*   2/2019   Santamaria ............ A61K 47/60

FOREIGN PATENT DOCUMENTS

WO          2012121528          9/2012

OTHER PUBLICATIONS

Pegylation as a Strategy for Improving Nanoparticle-Based Drug and Gene Delivery, Advanced Drug Delivery Rev, 99(Pt A): 28-51. (Year: 2016).*
Targeting Strategies for Multifunctional Nanoparticles in Cancer Imaging and Therapy, Theranostics, 2(1), 3-44. (Year: 2012).*
Castillo et al., "PEGylated versus non-PEGylated magnetic nanoparticles as camptothecin delivery system", Beilstein Journal of Nanotechnology, vol. 5, 2014, pp. 1312-1319.

* cited by examiner

*Primary Examiner* — Carlos A Azpuru
(74) *Attorney, Agent, or Firm* — Kilpatrick Townsend & Stockton LLP (57) ABSTRACT

A composition and methods of use and preparation are provided. The composition may comprise a magnetic nanoparticle comprising: a passivation layer; and at least one unique entity that is attached to the magnetic nanoparticle. For example, the composition may include a magnetic nanoparticle and an antibody attached to the magnetic nanoparticle. Such magnetic nanoparticle architecture can provide treatment by, and screening of, nanoparticles functionalized with various functional species.

18 Claims, 3 Drawing Sheets

PASSIVATED MAGNETIC NANOPARTICLES FOR CELL TARGETING AND METHODS OF PREPARATION AND USE

BACKGROUND

Uses of magnetic nanoparticles (MNPs) in vivo and/or in vitro are limited by such undesirable characteristics as poor colloidal stability, rapid opsonization and clearance by mononuclear phagocyte systems (MPS), poor targeting to cellular receptors, and nonspecific biofouling. Current methods for making magnetic nanoparticles employ a basic method for grafting poly(ethylene glycol) (PEG) moieties onto MNP surfaces (referred to as "PEGylation"), so as to reduce biofouling. However, current methods, such as attaching PEG to carboxylic acids on the surface of the nanoparticles using carbodiimide cross-linking chemistry, do not achieve sufficient PEG density to obtain a PEG "brush" layer, a dense layer in which the PEG chains extend away from the surface and provide optimal defense against opsonization, MNP colloid stability, and ample attachment sites for functionalization. Instead, the methods in use today result in a "mushroom" configuration of PEG, which promotes nonspecific binding.

It is therefore desirable to be able to sufficiently graft MNPs with a PEG passivation layer in a manner that allows for MNP functionalization, stability, targeting specificity, and anti-biofouling.

SUMMARY

The present disclosure provides novel functionalized magnetic nanoparticles and methods of using and making them. The functionalized magnetic nanoparticle provided herein is passivated with a PEG layer attached to a functional moiety (e.g., a targeting moiety). The functionalized magnetic nanoparticle comprises a magnetic nanoparticle encapsulated by a poly(ethylene glycol) (PEG) passivation layer, wherein the PEG passivation layer comprises PEG in a density of at least about 50 picomoles per centimeter squared (pM/cm$^2$). The PEG comprises at least one attachment site, and a first chemical attachment moiety is attached to the at least one attachment site of the PEG. Additionally, a second chemical attachment moiety is attached to the first chemical attachment moiety and to a functional moiety. The chemical attachment moieties are optionally click chemistry reagents that provide specific and controllable bioorthogonal binding. Also provided are compositions of a plurality of the functionalized magnetic nanoparticles. Such compositions are useful in vivo or in vitro.

Also provided herein are methods of making functionalized magnetic nanoparticles, including functionalized magnetic nanoparticles with a dense PEG passivation layer. By way of example, such a method comprises the steps of providing a carboxylated magnetic nanoparticle; reacting the carboxylated magnetic nanoparticle with 1-ethyl-3-(3-dimethylaminopropyl)carbodiimide and sulfonated N-hydroxysuccinimide to provide N-hydroxysuccinimide coated magnetic nanoparticles; and covalently linking (binding) poly(ethylene glycol) (PEG) in a surface activating solution (e.g., a high salt solution or an organic solvent solution) to the N-hydroxysuccinimide coated magnetic nanoparticles under conditions that provide a PEG density of at least about 50 pM/cm$^2$ on the magnetic nanoparticles. The PEG optionally includes at least one attachment site, and the method optionally includes attaching a first chemical moiety to the at least one attachment site on the PEG and attaching a second chemical moiety to the first chemical moiety, wherein the second chemical moiety is attached to a functional moiety.

A method of administering a functional moiety to a subject or a cell is also provided. The method comprises administering to the subject or cell one or more functionalized magnetic nanoparticles.

Other objects, advantages and features of the present disclosure will become apparent from the following specification taken in conjunction with the accompanying drawings.

BRIEF DESCRIPTION OF THE DRAWINGS

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

DETAILED DESCRIPTION

I. Overview

The disclosure herein provides magnetic nanoparticles having a passivating surface coating, with the passivating surface coating having a high grafting density (e.g., at least about 50 pM/cm$^2$) and functional groups attached to the passivating surface coating. Without a passivating surface coat, magnetic nanoparticles suffer from several undesirable characteristics, including poor colloidal stability, rapid opsonization and clearance by the mononuclear phagocyte system (MPS) in vivo, poor targeting to cellular receptors, and nonspecific biofouling. However, many of these problems can be improved by coating the surface of the particle with a dense layer of a hydrophilic polymer like polyethylene glycol (PEG), the industry standard for surface coatings to avoid biofouling. Although techniques exist to attach a PEG layer to particles, the existing methods fail to provide the level of PEG density required for optimal passivation. Disclosed herein is a method that increases PEG grafting density on the surface of magnetic particles. The resulting particles, coupled with one or more bioorthogonal click chemistry attachment sites (or handles), provide, in addition to reduced biofouling, improved amounts of attached functional moieties and improved binding to cellular receptors.

Also provided are in vivo and in vitro uses of the functionalized particles. Methods for treating or preventing a disease or condition in a subject are provided whereby the functionalized particles are administered to the subject. Optionally, the functionalized particles are administered in vitro to cells in culture. The cells treated with the functionalized particles are optionally then administered to a subject.

II. Particles and Compositions

The present disclosure provides a functionalized magnetic particle (e.g., a nanoparticle). The functionalized magnetic particle has a magnetic particle center and a PEG passivation layer. The PEG passivation layer is optionally linked to the magnetic particle center by an amide bond. The PEG passivation layer comprises at least about 50 picomoles/cm$^2$ (pM/cm$^2$) of PEG. In addition to the particle attachment site that binds the PEG to the particle, the PEG in the passivation layer comprises at least one attachment site attached to a first chemical attachment moiety. A functional moiety is attached to PEG by a second chemical attachment moiety, which is attached to the first chemical attachment moiety.

In some cases, after passivation the surface of the particle is hydrophobic. In some cased, the surface of the particle is hydrophilic after passivation.

The particles disclosed herein can be nanoparticles but also can be microparticles. Thus, when nanoparticle is recited herein, it is understood that a slightly larger particle (e.g., a microparticle) is suitable as well, depending on the particular use. In either case, the particle is made of any suitable material that is biocompatible and/or biodegradable. In some embodiments, the nanoparticle can be a magnetic particle comprising a cobalt particle, a nickel particle, or an iron oxide particle. In some embodiments, the nanoparticle can be a hollow core, a quantum dot, or an inorganic particle such as a silica particle, a porous silica particle, or a calcium phosphate particle, wherein such non-magnetic nanoparticles further include magnetic metal atoms chelated to the surface of the non-magnetic nanoparticle, providing a magnetic nanoparticle. Whenever magnetic particle is recited herein it is to be understood that non-magnetic particles are also suitable, depending on the specific use.

The particle can be of any shape, including but not limited to, sphere, square, rectangle, triangle, circular disc, cuboid shape, cube, rectangular parallelepiped, cone, cylinder, prism, pyramid, right-angled circular cylinder, and other regular or irregular shapes. Optionally, the diameter of the nanoparticle can be about 1-999 nm, including, for example, about 50 nm to about 500 nm. Optionally the diameter of a microparticle is 1-999 µm, for example, about 50 µm to about 500 µm.

Functionalized magnetic nanoparticles as provided herein can be of any suitable magnetic composition, including, but not limited to, iron-based nanoparticles, nickel-based nanoparticles, cobalt-based nanoparticles, certain lanthanoid nanoparticles, certain actinoid nanoparticles, certain transition metal nanoparticles, certain post-transition metal nanoparticles, certain metal-chelated non-magnetic nanoparticles, magnetic core—non-magnetic shell core-shell nanoparticles, non-magnetic core—magnetic shell core-shell particles, or the like.

As discussed above, the density of the PEG encapsulating the particle is at least about 50 picomoles/cm$^2$, for example, 50, 60, 70, 80, 90, or 100 pM/cm$^2$. In other words, the surface area of the passivation layer as it surrounds the particles has a PEG density of 50 pM/cm$^2$. As used herein, encapsulating is not meant to suggest a continuous layer; rather, the passivation layer of PEG, may comprise islands of PEG around the core particle.

The first and second chemical attachment moieties bind by specific and controllable bioorthogonal reactions to each other, for example, using click chemistry binding pairs. Binding pairs used in click chemistry or other binding reactions characterized by a high thermodynamic driving force that drives the reaction quickly and irreversibly to a single reaction product with high specificity can be used to bind a functional moiety to the PEG passivation layer. Provided herein is a functionalized magnetic nanoparticle wherein an attached PEG has a plurality of different or a plurality of similar click handles. Optionally, the PEG has multiple different or multiple similar functional moieties attached to it via the click handles. Additionally, each functional moiety may include elements with different functions. The functionalized magnetic nanoparticles disclosed herein can thus have at least one function, but may have multiple functions. Thus, in certain aspects, each of the functionalized magnetic nanoparticles may further comprise additional chemical attachment sites and may comprise additional functional moieties.

Examples of binding pairs include Tetrazine (Tz)/Trans-Cyclooctene (TCO), biotin/avidin or strepavidin, azide/alkyne, carboxylic acid/amine, thiol/maleimide, a hydrazine or hydroxylamine/carbonyl, a phosphine/azide (Staudinger Ligation), tetrazole/alkene, and the like. The first chemical attachment moiety (e.g., on the PEG) can be Tz, azide, biotin, carboxylic acid, thiol, hydrazine, phosphine, or a tetrazole; and the second chemical attachment (e.g., on the functional moiety) can be TCO, alkyne, avidin or streptavidin, an amine, a maleimide, a carbonyl, or an alkene. Alternatively, the first chemical attachment moiety can be TCO, alkyne, avidin or streptavidin, an amine, a maleimide, a carbonyl, or an alkene, and the second chemical attachment can be Tz, azide, biotin, a carboxylic acid, a thiol, a hydrazine, a phosphine, or a tetrazole. Optionally, the selected bound pairs are physiologically stable and non-toxic.

The functional moiety is selected based on the intended use of the functionalized particles, and a variety of functional moieties can be used depending upon the intended use. For example, the functionalized moiety can be a targeting agent, a therapeutic agent, an imaging agent, an enzyme, and any combination thereof. The functional moiety optionally recognizes specific biological targets (e.g., certain cells or receptors or other biomolecules) present in vivo or in vitro. The functional moiety can be a small molecule or a biologic agent and can be a naturally occurring or non-naturally occurring agent. Optionally, the functional moiety is an antibody or a fragment thereof or a chimeric molecule with multiple functions (e.g., with a targeting moiety, a therapeutic agent, and/or a label). Optionally the functional moiety specifically binds a selected cell type, e.g., a neoplastic cell.

The term antibody or fragments thereof, as used herein, encompasses IgG, IgA, IgM, IgD, IgE, as well as single chain variable fragment (scFv), chimeric antibodies and hybrid antibodies, with dual or multiple antigen or epitope specificities, and fragments, such as F(ab')2, Fab', Fab, and the like, including hybrid fragments. Thus, fragments of the antibodies that retain the ability to bind their specific targets can be attached to the functionalized particles. For example, fragments of antibodies which maintain binding activity for a neoplastic cell are included within the meaning of the term antibody or fragment thereof. Such antibodies and fragments can be made by techniques known in the art and can be screened for specificity and activity according to general methods for producing antibodies and screening antibodies for specificity and activity (See Harlow and Lane, Antibodies: A Laboratory Manual, Cold Spring Harbor Publications, New York (1988)). Also included within the meaning of antibody or fragments thereof are conjugates of antibody fragments and antigen binding proteins (single chain antibodies) as described, for example, in U.S. Pat. No. 4,704,692, the contents of which are hereby incorporated by reference in their entirety.

Optionally, the antibody attached to the functionalized fragment is a monoclonal, human or humanized antibody. The term monoclonal antibody as used herein refers to an antibody from a substantially homogeneous population of antibodies, i.e., the individual antibodies comprising the population are identical except for possible naturally occurring mutations that may be present in minor amounts. Monoclonal antibodies may be prepared using hybridoma methods, such as those described by Kohler and Milstein, Nature, 256:495 (1975) or Harlow and Lane, Antibodies: A Laboratory Manual, Cold Spring Harbor Publications, New York (1988). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

Optionally the functional moiety includes a label. The label can be, by way of example, a chromogenic label (e.g., alkaline phosphatase (AP) or horseradish peroxidase (HRP) for enzymatic visualization), a fluorescent label (e.g., FITC or the like), a radioactive label, or other contrast agent conjugated directly to the functionalized nanoparticle. Optionally, the functionalized nanoparticle is unlabeled but can be indirectly labeled using, for example, a secondary or tertiary antibody that is labeled. Optionally, the particles can quantified by mass cytometry, mass spectroscopy, multiplexed ion beam imaging, fluorescence spectroscopy, absorption spectroscopy, confocal microscopy, three-dimensional (3D) laser microscopy, laser capture microscopy, any suitable optical analytical technique, or any combination thereof. Optionally, the particles or labels attached thereto (directly or indirectly) can be visualized in a subject using any of a variety of imaging methods, e.g., x-ray, CT-scan, ultrasound, nuclear scan, fluorescence spectroscopy, radioactive tracers, magnetic resonance imaging (MRI), and ultrasound.

In some embodiments, the magnetic nanoparticle comprises a releasable payload. The releasable payload can include a therapeutic agent, a label, a prognostic agent, an imaging agent, or a combination thereof. The releasable payload can be bound to or encapsulated in the magnetic nanoparticle.

Also provided herein is a composition comprising a plurality of one or more functionalized magnetic nanoparticles. The nanoparticles in the composition may have the same or different chemical binding entities, same or different functional moieties, same or different particles, etc. Optionally the composition is a pharmaceutical composition comprising an effective amount of functionalized magnetic nanoparticles as described herein with a pharmaceutically acceptable carrier.

As used herein, a pharmaceutical composition is a composition comprising an effective amount of a plurality of functionalized particles and a pharmaceutical carrier, optionally with other medicinal agents or diluents. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. As used herein, pharmaceutically acceptable is meant that a material that is not biologically or otherwise undesirable, which can be administered to an individual along with the particle without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, or other material known in the art for use in pharmaceutical formulations. The choice of a carrier for use in a composition will depend upon the intended route of administration for the composition. The preparation of pharmaceutically acceptable carriers and formulations containing these materials is described in, e.g., Remington: The Science and Practice of Pharmacy, 22nd edition, Loyd V. Allen et al, editors, Pharmaceutical Press (2012). Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

Compositions containing the functionalized particles described herein suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof are admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethylene glycols, and the like.

Solid dosage forms such as tablets, dragées, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, such as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, sesame oil, glycerol, tetrahydrofurfuryl alcohol, polyethylene glycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Also provided is a medicament delivery system. The system is optionally provided as a delivery container (e.g., a vial, a syringe, an intravenous bag, or the like) and an effective amount of a composition comprising a plurality of the functionalized magnetic nanoparticles, optionally dispersed in a physiologically acceptable carrier.

A diagnostic or imaging composition comprising functionalized magnetic nanoparticles with a selected label is provided. The selected label can be a luminescent molecule (e.g., a fluorescent molecule, photoluminescent molecule and/or electroluminescent molecule). Optionally the composition includes one or more contrast agents or a carrier.

A library comprising a plurality of populations of nanoparticles is provided herein. The library optionally contains various functionalized nanoparticles. Variable factors across the library can include one or more of size and/or composition of the particles; PEG attachments to the particles; number and type of functional moieties; number and type of binding partners between PEG and the functional molecule; labels; etc.

In certain embodiments, the nanoparticle supports an outer surface coating that may be included as part of the nanoparticles. The diameter of the nanoparticle can be about 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 micron, 2 microns, 3 microns, 4 microns, 5 microns, 6 microns, 7 microns, 8 microns, 9 microns, or 10 microns, or any suitable sub-ranges within the about 10 nm to about 10 micron range, e.g., a diameter from about 50 nm to about 150 nm. Generally, the nanoparticle can have a diameter from about 10 nm to about 10 microns. In certain embodiments, the nanoparticle of the composition has a diameter from about 50 nm to about 500 nm.

III. Methods of Making Functionalized Particles

The present disclosure further provides methods of making functionalized magnetic nanoparticles for in vitro and in vivo applications. The method includes making a plurality of magnetic nanoparticles, each magnetic nanoparticle comprising a high density passivation layer, optionally by converting carboxylic acid groups on the surface of the magnetic nanoparticle to a reactive N-hydroxysuccinimide (NHS) attachment site attaching a heterobifunctional PEG in the presence of a surface activating solution to provide a high grafting density PEG passivation layer. Optionally the PEG used in these methods comprises a chemical attachment site (referred to as a "click handle"), and a functional moiety is attached via "click chemistry" (e.g., any one of azide-alkyne cycloaddition reactions, alkyne-nitrone cycloaddition reactions, alkene-azide cycloaddition reactions, alkene-tetrazole photocatalyzed reactions, and alkene-tetrazine Diels-Alder+cycloaddition reactions).

Figure 1:
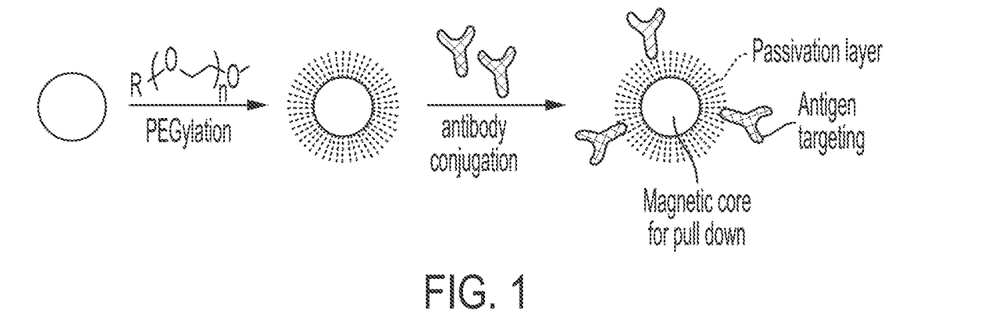
FIG. 1 is a schematic showing a general PEGylation and antibody conjugation method.

A general procedure is depicted in FIG. 1, whereby an antibody is conjugated to a PEGylated particle. The method of making a functionalized magnetic nanoparticle comprises the steps of providing a carboxylated magnetic nanoparticle; reacting the carboxylated magnetic nanoparticle with carbodiimide reagents such as 1-ethyl-3-(3-dimethylaminopropyl)carbodiimide or DCC and sulfonated N-hydroxysuccinimide to provide N-hydroxysuccinimide coated magnetic nanoparticles; or, alternatively, a hydroxybenzotriazole reagent like HATU (1-[Bis (dimethylamino)methylene]-1H-1,2,3-triazolo[4,5-b]pyridinium-3-oxid hexafluorophosphate) with sulfo-NHS in the presence of an amine base can be employed; and covalently linking poly(ethylene glycol) (PEG) in a surface activating solution to the N-hydroxysuccinimide coated magnetic nanoparticles under conditions that provide a PEG density of at least about 50 picomoles/$cm^2$.

Figure 2:
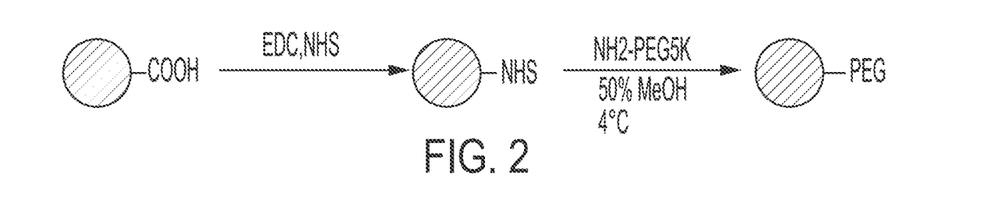
FIG. 2 is a schematic showing high density PEGylation via a two-step carbodiimide chemistry reaction. The carbodiimide, 1-ethyl-3-(-3-dimethylaminopropyl) carbodiimide hydrochloride (EDC), is coupled to the magnetic nanoparticles in the presence of Sulfo-NHS, and PEG is conjugated to the amine group in the presence of methanol at 4° C.
Figure 3:
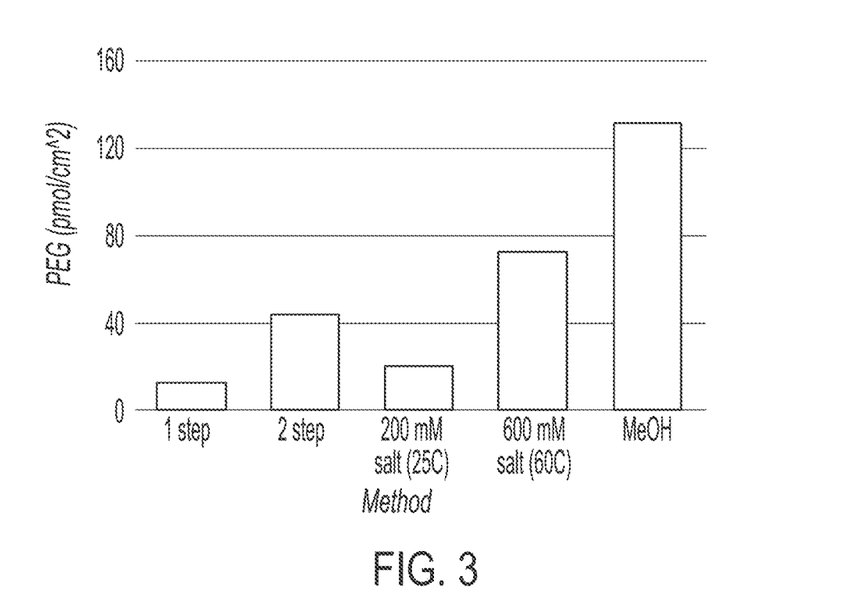
FIG. 3 is a graph showing the density of PEG on commercially available magnetic particles using various methods: one step and two step carbodiimide using standard procedures, low salt (200 mM) at 25° C., increased salt (600 mM salt) at 60° C., and in cold methanol.

As described herein, achieving a high density of PEG in the passivation layer provides optimized function. The desired level of density can be achieved with various surface activating solutions (e.g., organic solvent solution or high salt aqueous solutions) and conditions. An example of a two-step carbodiimide binding step for covalently attaching PEG to the particle is shown in FIG. 2. FIG. 2 shows use of a 50% methanol solution as the surface activating solution and 4° C. as the condition used to bind the PEG to the particle. In addition, methanol solutions of at least 50% and temperatures of 1-10° C. are also effective for achieving the desired PEG density on the nanoparticle. Also effective for achieving the desired density is a high salt aqueous solution used as the surface activating solution. Thus the step for attaching PEG to the particle is optionally performed in the presence of a high salt solution and temperatures of 20-80° C. FIG. 3 shows comparative results for PEGylation with a one-step or two step carbodiimide without high salt or methanol, with 200 mM salt at 25° C., 600 mM salt at 60° C., and with methanol at 4° C. With optimized conditions, the density can be increased up to about 3 fold as compared to the traditional 1 step and 2 step methods known in the art.

A PEG passivation layer can be formed by a mixture of PEG chains, for example, amine-PEG (where the PEG was either heterobifunctional, with an attachment site on the other terminus, or methoxy-terminated), and amine-PEG-Tetrazine (Tz). The mixture of PEG chains can be simultaneously attached to the particle in a one-pot reaction. Additionally, the mixture of PEG chains can be prepared at various ratios (e.g., 1:1, 9:1, etc.) to tailor the surface characteristics of the particle. For example, the mixture of PEG chains can be prepared at a ratio of 1:1, 2:1, 3:1, 4:1, 5:1, 6:1, 7:1, 8:1, 9:1, 10:1, 20:1, 30:1, 40:1, 50:1, 60:1, 70:1, 80:1, 90:1, 100:1, 200:1, 300:1, 400:1, 500:1, 600:1, 700:1, 800:1, 900:1, 1000:1, 2000:1, 3000:1, 4000:1, 5000:1, 6000:1, 7000:1, 8000:1, 9000:1, 10000:1, 20000:1, 30000:1, 40000:1, 50000:1, 60000:1, 70000:1, 80000:1, 90000:1, $1\times10^5$:1, $1\times10^6$:1, $1\times10^7$:1, $1\times10^8$:1, $1\times10^9$:1, anywhere in between, or any suitable ratio.

Figure 5:
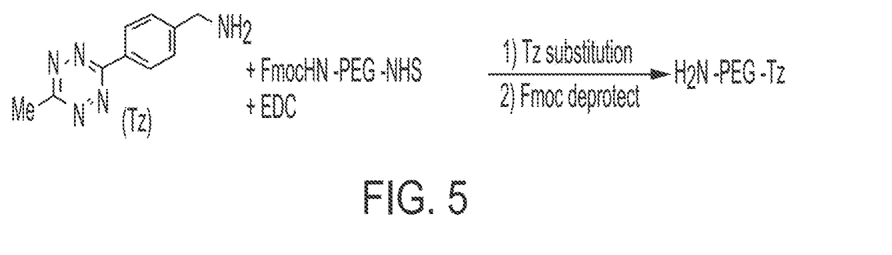
FIG. 5 is a schematic showing a reaction scheme for synthesis of a heterobifunctional PEG with amine and tetrazine attachment sites.
Figure 6:
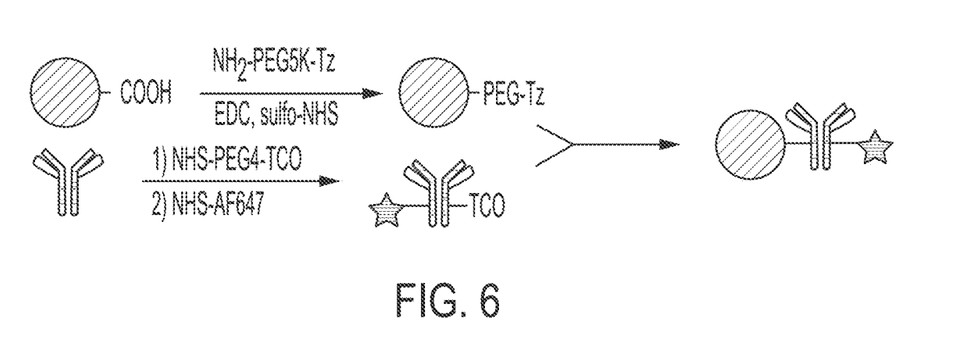
FIG. 6 is a schematic showing a general procedure for attachment of a targeting group such as an antibody to the PEGylated particle.

The methods of making the functionalized particles as described herein optionally further comprise attaching a first chemical moiety to the at least one attachment site on the PEG and attaching a second chemical moiety to the first chemical moiety, wherein the second chemical moiety is attached to a functional moiety (e.g., an antibody). Thus, in addition to attaching an amine to PEG for binding it to the particle, as described above, an attachment site can be added to PEG for attaching the PEG to a functional moiety. FIG. 5 shows an example of how PEG is converted to a heterobifunctional-PEG with both an amine and a tetrazine handle. The tetrazine handle, or other click chemistry moiety as described herein, is bound to the PEG and the functional moiety, which is bound to the appropriate click partner is used to bind the functional moiety to the PEG. An exemplary procedure is depicted in FIG. 6.

Briefly, by way of example, a bifunctional PEG is modified at the NHS terminus by methyltetrazine-amine (Tz-amine). The reaction is carried out with 1 equivalent of Fmoc-PEG-NHS, 3 equivalents of Tz-amine, and 1 equivalent of EDC in dry dimethylformamide (DMF) under dry nitrogen. This step can also be performed using 1 equivalent 1-[Bis(dimethylamino)methylene]-1H-1,2,3-triazol[4,5-b]pyridinium 3-oxid hexafluorophosphate, N-[(Dimethylamino)-1H-1,2,3-triazolo-[4,5-b]pyridin-1-ylmethylene]-N-methylmethanaminium hexafluorophosphate N-oxide (HATU) to improve efficiency and to mitigate any NHS hydrolysis. The PEG can be precipitated with ether to obtain pink solids. After the tetrazine has been conjugated, 10% piperidine in DMF is used to deprotect the amine. The resulting product PEG construct is purified by precipitation with ether and used for conjugation to magnetic nanoparticles. Conjugation of a targeting group like an antibody is carried out using an incorporated click chemistry handle like a tetrazine. The antibody or other targeting group is modified with the corresponding click handle, such as a trans-cyclooctene for tetrazine-transcyclooctene click. This click pair has the advantage of limited lipophilicity and higher reaction rates. The modification to the antibody can be achieved specifically (hinge region modification, C- or N-terminus modification, or via site-click sugar modification) or nonspecifically using lysine chemistry. The antibody and particles are combined in a vial for the click reaction and are covalently and irreversibly linked. In another variation, an alternative click pair such as DBCO-azide or alkyne-azide could also be used, with one click partner residing on the PEG chain and the other residing on the targeting group of interest. Thus, the magnetic nanoparticle is subjected to PEGylation and functional species (e.g., antibodies) are attached to the PEG molecules via an attachment site on the PEG molecules to produce a passivated functionalized magnetic nanoparticle.

IV. Methods of Using Particles or Compositions

The functionalized particles described herein are useful in vivo or in vitro. For in vivo uses, the method may include administering to the subject an effective amount of any of the functionalized particles or compositions comprising the functionalized particles disclosed herein. Thus, provided herein is a method of administering a functional moiety to a subject comprising administering to the subject one or more functionalized magnetic nanoparticles or composition containing the nanoparticles as described herein.

Provided herein is a method of treating a subject with a disease or disorder with an effective amount of a functional moiety by administering to the subject in need the functionalized particles described herein. As discussed herein, functionalized nanoparticles may be used as pharmaceutical compositions, medicament delivery systems, and/or imaging systems in the treatment or diagnosis of a variety of disorders or diseases including, for example, cancer, ocular diseases or conditions, pulmonary diseases or conditions, cardiac diseases or conditions, infectious disease, a parasitic disease, immune disorder, endocrine disease or disorder, a neural disease or disorder, a gastrointestinal disease or disorder, a musculoskeletal disease or disorder, and/or a genitourinary disease or disorder.

In certain methods, the functionalized particle comprises a therapeutic agent that is delivered to the cell surface or delivered intracellularly. When the functionalized particle includes a targeting moiety and a therapeutic agent, the therapeutic payload is delivered selectively to the target cell.

In some embodiments, the present functionalized particles or pharmaceutical compositions are used to deliver the exemplary medications listed in the Orange Book: Approved Drug Products with Therapeutic Equivalence Evaluations, published by the U.S. Food and Drug Administration, the exemplary medications listed in The Merck Index (a U.S. publication, the printed 14th Edition, Whitehouse Station, N.J., USA) and its online version (The Merck Index Online$^{SM}$), and the exemplary medications listed in Biologics Products & Establishments published by the U.S. Food and Drug Administration, and can be used to treat or prevent the corresponding diseases and disorders.

For in vivo method, the particles or compositions are administered in a number of ways depending on whether local or systemic treatment is desired, and on the area to be treated. The particles or compositions are administered via any of several routes of administration, including orally, parenterally, intravenously, intraperitoneally, intramuscularly, subcutaneously, intrarectally, intracavity, transdermally, intraventricularly, or transvertebrally (i.e., into the cerebrospinal fluid). Pharmaceutical compositions can also be delivered locally to the area in need of treatment, for example by local injection. Effective doses for any of the administration methods described herein can be extrapolated from dose-response curves derived from in vitro or animal model test systems.

One of skill in the art can determine the proper dosing regimen based on a number of factors, including intended use (e.g., imaging, diagnosis, treatment). The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the activity of the specific compound employed, the metabolic stability and length of action of that compound, the species, age, body weight, general health, sex, and diet of the subject, the mode and time of administration, rate of excretion, drug combination, and severity of the particular condition, and can be determined by one of skill in the art. The dosage can be adjusted by the individual physician in the event of any contraindications. Dosages can vary, and can be administered in one or more dose administrations daily, for one or several days.

For in vitro uses, cells in culture are contacted with functionalized particles or compositions containing the particles as described herein. In certain methods, cells contacted with the functionalized particles or compositions comprising them can then be administered to a subject. Such cells can be derived from the same subject or a different subject and can be, for example, stem cells or other pluripotent cells. One of skill in the art could determine an effective dosing regimen for in vitro use. For in vitro use, such dosing regimen can include multiple doses over minutes, hours, days, or weeks and the amount of each dose is determined based on multiple factors, such as the size of the culture dish or well, the concentration of cells in the dish or well, the stability of the functional moiety, the amount of culture medium, and the dilution of the functionalized particles upon addition to the culture medium.

Administration of the particles or composition comprising the particles allows for the particles or functional moiety to bind to a cell membrane protein or sugar moiety, or to cross the cell membrane of the cell, in vivo or in vitro.

Optionally, the particles used in the methods comprise a functional moiety that is selected from a targeting moiety, a therapeutic agent, an imaging agent, or any combination thereof. In certain methods, the functionalized particle includes a targeting moiety specific for a specific cell type or cell membrane protein or sugar moiety. By way of example, the targeting moiety can be specific for neoplastic cells or a specific cellular membrane protein on a neoplastic cell. In such case, the functionalized particles are useful for the identification of a neoplasm in a subject. In certain embodiments, where the particle comprises a marker, label, or imaging agent, the particles administered to the subject or to a culture of cells are subsequently detected.

Optionally, the method further comprises quantification of particles (bound or unbound to target cells) using mass cytometry, mass spectroscopy, multiplexed ion beam imaging, fluorescence spectroscopy, absorption spectroscopy, confocal microscopy, three-dimensional (3D) laser microscopy, laser capture microscopy, any suitable optical analytical technique, or any combination thereof. Optionally, the method comprises detecting a marker or label on the nanoparticles (bound or unbound) in a subject using any of a variety of imaging methods, e.g., x-ray, CT-scan, ultrasound, nuclear scan, magnetic resonance imaging (MRI), and ultrasound.

In some non-limiting embodiments, employing magnetic nanoparticles as described herein includes manipulation of the magnetic nanoparticles. Magnetic forces can be employed to control position, flow direction, flow rate, and other various location aspects of the magnetic nanoparticles.

The present nanoparticles can be used to evaluate performance of or refine medicament delivery systems, pharmaceutical compositions, and methods used to treat or prevent conditions or diseases. Functionalized magnetic nanoparticle can be used to evaluate targeting, efficiency, biological performance, and pharmacokinetics (PK) of medicament delivery systems and pharmaceutical compositions.

As described herein, magnetic nanoparticles can be administered to cells in vivo or in vitro. Magnetic nanoparticles can provide high variation of traceable signals further providing identification of individual marked magnetic nanoparticle types from a complex mixture (e.g., by determining the PK of many different formulations from a single co-administration of a plurality of marked magnetic nanoparticles in a single sample or subject). The monitoring may comprise mass cytometry, mass spectroscopy, fluorescence spectroscopy, absorption spectroscopy, optical microscopy, or any combination thereof. In various embodiments, the monitoring provides high-throughput screening of pluralities of magnetic nanoparticles targeting pluralities of specific cell lines.

There are a number of advantages associated with the compositions and methods of the present disclosure. First, the method allows for highly multiplexed in vivo studies of magnetic nanoparticles. Without multiplexing, each nanoparticle type would need to be tested in vivo separately, thereby requiring large capital expenditures and time investment. Multiplexing allows many particles to be tested in parallel within a single experiment. Second, multiplexing allows for combinatorial experiments to be performed in which various surface functionalizations can be mixed at varying quantities to endow each magnetic nanoparticle with a unique "fingerprint" that may confer emergent function to the magnetic nanoparticle that could not have been predicted from the individual functions of magnetic nanoparticles coated with one type of functional group.

V. Definitions

The practice of the present disclosure will employ, unless otherwise indicated, conventional techniques of nanotechnology, nano-engineering, molecular biology (including recombinant techniques), microbiology, cell biology, biochemistry, immunology, and pharmacology, which are within the skill of the art.

Unless defined otherwise, all technical and scientific terms used herein have the same meaning as is commonly understood by one of ordinary skill in the art to which this disclosure belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

To facilitate understanding of the disclosure, a number of terms and abbreviations as used herein are defined below as follows:

The term and/or when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

The term "nanoparticle" as used herein refers to nanostructure, particles, vesicles, or fragments thereof having at least one dimension (e.g., height, length, width, or diameter) of between about 1 nm and about 10 microns. For systemic use, an average diameter of about 50 nm to about 500 nm, or 100 nm to 250 nm may be preferred. The terms "nanostructure" includes, but is not necessarily limited to, particles and engineered features. The particles and engineered features can have, for example, a regular or irregular shape. Such particles are also referred to as nanoparticles. The nanoparticles can be composed of organic materials or other materials, and can alternatively be implemented with porous particles. The layer of nanoparticles can be implemented with nanoparticles in a monolayer or with a layer having agglomerations of nanoparticles. As used herein, a nanoparticle having an inner core may be covered by an outer surface comprising the membrane as discussed herein. The disclosure contemplates any nanoparticles now known and later developed that can be coated with the membrane described herein.

In various embodiments, the cellular membrane covering either of the unilamellar or multilamellar nanoparticles can be further modified to be saturated or unsaturated with other lipid components, such as cholesterol, free fatty acids, and phospholipids, also can include endogenous or added proteins and carbohydrates, such as cellular surface antigen. In such cases, an excess amount of the other lipid components can be added to the membrane wall which will shed until the concentration in the membrane wall reaches equilibrium, which can be dependent upon the nanoparticle environment. Membranes may also comprise other agents that may or may not increase an activity of the nanoparticle. In other examples, functional groups such as antibodies and aptamers can be added to the outer surface of the membrane to enhance site targeting, such as to cell surface epitopes found in cancer cells. The membrane of the nanoparticles can also comprise particles that can be biodegradable, cationic nanoparticles including, but not limited to, gold, silver, and synthetic nanoparticles.

The terms pharmaceutically active as used herein refers to the beneficial biological activity of a substance on living matter and, in particular, on cells and tissues of the human body. A pharmaceutically active agent, therapeutic agent, or drug is a substance that is pharmaceutically active and a pharmaceutically active ingredient (API) is the pharmaceutically active substance in a drug. The API can be a small molecule or a biologic agent.

The term pharmaceutically acceptable as used herein means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

The terms pharmaceutically acceptable salt as used herein refer to acid addition salts or base addition salts of the compounds, such as the multi-drug conjugates, in the present disclosure. A pharmaceutically acceptable salt is any salt which retains the activity of the parent compound and does not impart any deleterious or undesirable effect on a subject to whom it is administered and in the context in which it is administered.

Pharmaceutically acceptable salts may be derived from amino acids including, but not limited to, cysteine. Methods for producing compounds as salts are known to those of skill in the art (see, for example, Stahl et al., Handbook of Pharmaceutical Salts: Properties, Selection, and Use, Wiley-VCH; Verlag Helvetica Chimica Acta, Zurich, 2002; Berge et al., J. Pharm. Sci. 66: 1, 1977, which are incorporated by reference in its entirety). In some embodiments, a pharmaceutically acceptable salt is intended to mean a salt of a free acid or base of a compound represented herein that is non-toxic, biologically tolerable, or otherwise biologically suitable for administration to the subject. See, generally, Berge, et al., J. Pharm. Sci., 1977, 66, 1-19. In general, pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenyl acetates, phenylpropionates, phenylbutyrates, citrates, lactates, gamma-hydroxybutyrates, glycolates, tartrates, and mandelates.

The term pharmaceutically acceptable carrier as used herein refers to an excipient, diluent, preservative, solubilizer, emulsifier, adjuvant, and/or vehicle with which a compound, such as a multi-drug conjugate, is administered. Such carriers may be sterile liquids, such as water and oils, including those of petroleum, animal, vegetable or synthetic origin, such as peanut oil, soybean oil, mineral oil, sesame oil and the like, polyethylene glycols, glycerin, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language pharmaceutically acceptable carrier is intended to include pharmaceutically acceptable salts, as well as any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy, 20$^{th}$ ed., (Lippincott, Williams & Wilkins 2003). Except insofar as any conventional media or agent is incompatible with the active compound, such use in the compositions is contemplated.

As used herein, a subject or individual or a refers to an animal, a non-human mammal, or a human. A subject in need is a subject having a need for therapy, diagnosis, or other uses of the nanoparticles disclosed herein. As used herein, animals include a pet, a farm animal, an economic animal, a sport animal and an experimental animal, such as a cat, a dog, a horse, a cow, an ox, a pig, a donkey, a sheep, a lamb, a goat, a mouse, a rabbit, a chicken, a duck, a goose, and/or a primate, including a monkey and a chimpanzee. In some cases, the subject is a patient being treated for a specific condition.

As used herein, the term therapeutically effective amount refers to those amounts that, when administered to a particular subject in view of the nature and severity of that subject's disease or condition, will have a desired therapeutic effect, e.g., an amount which will cure, prevent, inhibit, or at least partially arrest or partially prevent a target disease or condition. More specific embodiments are included in the Pharmaceutical Preparations and Methods of Administration section below. In some embodiments, the term therapeutically effective amount or effective amount refers to an amount of a therapeutic agent that when administered alone or in combination with an additional therapeutic agent to a cell, tissue, or subject is effective to prevent or ameliorate the disease or condition, such as an infection or the progression of the disease or condition. A therapeutically effective dose further refers to that amount of the therapeutic agent sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously.

As used herein, treating or treatment or alleviation refers to therapeutic treatment wherein the object is to slow down (lessen), if not cure the targeted pathologic condition or disorder, or prevent recurrence of the condition. A subject is successfully treated if, after receiving a therapeutic amount of a therapeutic agent, the subject shows observable and/or measurable reduction in, or absence of, one or more signs and symptoms of the particular disease. Reduction of the signs or symptoms of a disease may also be felt by the patient. A patient is also considered treated if the patient experiences stablized disease progression. In some embodiments, treatment with a therapeutic agent is effective to result in the patients being disease-free 3 months after treatment, 6 months after treatment, one year after treatment, or 2 or more years after treatment. These parameters for assessing successful treatment and improvement in the disease are readily measurable by routine procedures familiar to a physician of appropriate skill in the art.

The term combination refers to either a fixed combination in one dosage unit form, or a kit of parts for the combined administration where a compound and a combination partner (e.g., another drug as explained below, also referred to as therapeutic agent or co-agent) may be administered independently at the same time or separately within time intervals, especially where these time intervals allow that the combination partners show a cooperative, e.g., synergistic, effect. The terms co-administration or combined administration or the like as utilized herein are meant to encompass administration of the selected combination partner to a single subject in need thereof (e.g., a patient), and are intended to include treatment regimens in which the agents are not necessarily administered by the same route of administration or at the same time. The term pharmaceutical combination as used herein means a product that results from the mixing or combining of more than one active ingredient and includes both fixed and non-fixed combinations of the active ingredients. The term fixed combination means that the active ingredients, e.g., a compound and a combination partner, are both administered to a patient simultaneously in the form of a single entity or dosage. The term non-fixed combination means that the active ingredients, e.g., a compound and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

Various aspects of this disclosure are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges as well as individual numerical values within that range, including any and all endpoints. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

VI. Abbreviations

MES=2-(N-Morpholino)ethanesulfonic acid, 4-Morpholineethanesulfonic acid monohydrate
PEG=Polyethylene glycol
EDC=N-(3-Dimethylaminopropyl)-N'-ethylcarbodiimide hydrochloride
COOH=Carboxylic Acid
NH2=Primary Amine
Tz=tetrazine
TCO=trans cyclooctene
MWCO=molecular weight cutoff
NHS=n-hydroxysuccinimide
PB=phosphate buffer
PBS=phosphate buffer solution
BSA=Bovine serum albumin
PF-127=Pluronic F-127

EXAMPLES

Example 1: Antibody-TCO Synthesis

Antibodies (IgG, FAB, scFV,) targeting a specific antigen, as well as a non-binding IgG control, (BioLegend) were nonspecifically decorated with click chemistry handles (such as TCO, azide, biotin, etc) in order to enable their conjugation to liposomes functionalized with their click partner. In an example using tetrazine (Tz) and strain promoted trans-cyclooctene (TCO) cycloaddition chemistry, antibodies (full length IgG) were nonspecifically modified with both TCO and with a fluorescent label to enable quantification of the degree of conjugation by fluorescence. TCO was incorporated by reacting 250 µL of 0.4 µg/mL antibody with 13.2 µM TCO-PEG4-NHS (purchased from Click Chemistry Tools) in 100 mM sodium bicarbonate and for one hour at room temperature. Excess TCO-PEG4-NHS was washed off using a 30 kDa MWCO centrifugal filter, using PBS for buffer exchange. The final concentration of protein was quantified using absorbance at 280 nm.

Example 2: Fluorescein Conjugation to Antibody-TCO Conjugate

Antibody-TCO conjugates were further modified with fluorescent dye. Antibody at ~0.4 µg/mL was combined with 1 M sodium bicarbonate to obtain a final buffer concentration of 100 mM sodium bicarbonate in PBS. To this solution, 1.2 µL of 3 mM Alexa Fluor 647-NHS (Thermo) was added and the resulting mixture was incubated at room temperature for 1 hour, protected from ambient light. Excess fluorophore was removed via filtration in a centrifugal filter, washing repeatedly with PBS. This procedure typically resulted in 4-7 fluorophore molecules per full length IgG antibody.

Example 3: Antibody Conjugation to Tz Particles

Antibody labeled with a click chemistry handle such as TCO and a fluorophore tracker (Alexa Fluor 647) was conjugated to the tetrazine particles by resuspending 500 µg of particles in 100 µL of antibody at 100-500 nM concentration. The reaction was rotated end to end at room temperature overnight, protected from ambient light. The particles were concentrated using a magnetic concentrator and excess reaction solution was removed. The particles were resuspended in PBS and washed repeatedly until excess antibody was removed. The particles were resuspended in PBS and quantified by nanoparticle tracking analysis (NTA) to determine size and concentration.

Example 4: Specific Binding of Magnetic Nanoparticles to Cells

Cell binding was carried out with two different human cell lines, one that over expresses a target antigen, EpCAM, and a control line that does not express the antigen. All cell binding was carried out with cells in suspension. A suspension of about 100,000 cells in 100 µL media was combined with nanoparticles until a final NP concentration of 5E9-1E11 NP/mL was obtained. This corresponded to $5\times10^4$-$1\times10^6$ NP per cell. The mixture was incubated at 37° C. for 1 hour, then unbound particles were removed by washing the cells in a 5 µm transwell plate, eluting with at least 1 mL of PBS buffer. Cell fluorescence was measured by flow cytometry using an Attune NxT Flow cytometer. Flow cytometry data was analyzed in FlowJo flow cytometry analysis software to determine the geometric mean or median as a quantitative comparison of the degree of binding by each sample to each cell type.

Example 5: Synthesis of Reagents: Tz-PEG(5K)

Tetrazine modification: Tetrazine-amine and NHS-PEG (5K)-amine-Fmoc (Fmoc protected amine) were purchased from Click Chemistry Tools and Nanocs, respectively. Tetrazine-amine and the NETS-PEG were combined in a 1:1 molar ratio in dry DMF at 20 mM concentration, in an air-free reaction vessel. An equimolar amount of dry triethylamine was added via syringe and the reaction was stirred at room temperature for 4 hours. The resulting Tz-PEG was precipitated via addition of cold diethyl ether. The precipitated pellet was then triturated with cold ether. This produced solid tetrazine-PEG(5 k)-amine-Fmoc.

Amine deprotection: Tetrazine-PEG(5 k)-amine-Fmoc was dissolved in DMF containing 10% piperidine. The reaction was stirred vigorously for 2 hours. Cold ether was added to precipitate the PEG, and the pellet was triturated further to remove ether-soluble side products. The solid was then dried under reduced pressure to produce a pink powder.

Tetrazine quantitation: The degree of tetrazine functionalization was determined using the absorbance of the tetrazine at 540 nm. A standard curve was prepared with methyl tetrazine in methanol to provide a linear fit. The absorbance of the tetrazine-PEG was then determined and the amount of tetrazine calculated relative to the total weight of the solid to provide a percentage of the PEGs that contained tetrazine. A typical reaction results in 30-40% tetrazine functionalization.

Example 6: Particle PEGylation with Methanol

Commercially available carboxylic acid-coated magnetic particles were first activated with EDC and sulfo-NHS in pH 4.6 MES buffer (100 mM MES, 0.9% NaCl, pH 4.6+0.3% PF-127) to produce NETS-activated particles. EDC (10 mg/mL) and sulfo-NHS (5 mg/mL) were combined in MES buffer and the particles were resuspended in this reaction buffer at a ratio of 10 mg particles to 500 µL of buffer. Particles were reacted at room temperature for 30 minutes, then washed once with MES buffer, once with pH 7.5 PB buffer (50-100 mM sodium phosphate, pH 7.5+0.3% PF-127), and once with 50-100% methanol at 4° C. Amine-PEG was dissolved in 50-100% cold methanol to obtain a solution at 10 mg/mL. The PEG solution was cooled to 4° C., then used to resuspend the NETS-modified nanoparticles in a particle:PEG ratio of 1:1 by weight. The reaction was carried out overnight at 4° C. in a rotator. After 18 hours at 4° C., PEGylated particles were washed three times with PBS or another desired storage buffer and stored at 4° C.

Example 7: Particle PEGylation with High Salt

Commercially available carboxylic acid-coated magnetic particles were first activated with EDC and sulfo-NHS in pH 4.6 MES buffer to produce NETS-activated particles. EDC (10 mg/mL) and sulfo-NHS (5 mg/mL) were combined in MES buffer and the particles were resuspended in this reaction buffer at a ratio of 10 mg particles to 500 µL of buffer. Particles were reacted at room temperature for 30 minutes, then washed once with MES buffer, once with pH 7.5 PBS, and once with 400-600 mM sodium sulfate in water. PEG was conjugated by dissolving 10 mg/mL of 5 k PEG-amine (where the PEG was either heterobifunctional, with a reactive handle on the other end, or methoxy-terminated) in 400-600 mM sodium sulfate solution, heating the solution to 60° C., and then resuspending the particle solution in the PEG-sodium sulfate solution at a ratio of 1 mg NHS particles to 100 µL of 10 mg/mL PEG solution. The reaction was carried out overnight at 60° C. in a tube shaker. After 18 hours, PEGylated particles were washed three times with phosphate buffer pH 7.4 or another desired storage buffer and stored at 4° C. for up to one month.

Example 8: BSA Adsorption Assay

5 μL of fluorescently labeled BSA at 20 mg/mL was added to 95 μL of the nanoparticle solution at $1 \times 10^{12}$ nanoparticles/mL. The sample was gently agitated at room temperature and protected from light to prevent photobleaching. Particle samples were washed four times by magnetic separation and resuspension to remove unbound BSA. A standard curve was prepared with a range of BSA concentrations and this standard curve and the particle samples were measured for their fluorescence of the fluorophore on the BSA. A linear fit to the standard curve was used to quantify the amount of BSA associated with the samples, adjusted for the fluorescence of non-BSA-treated nanoparticles.

Example 9: Optimizing PEG Density

Figure 4:
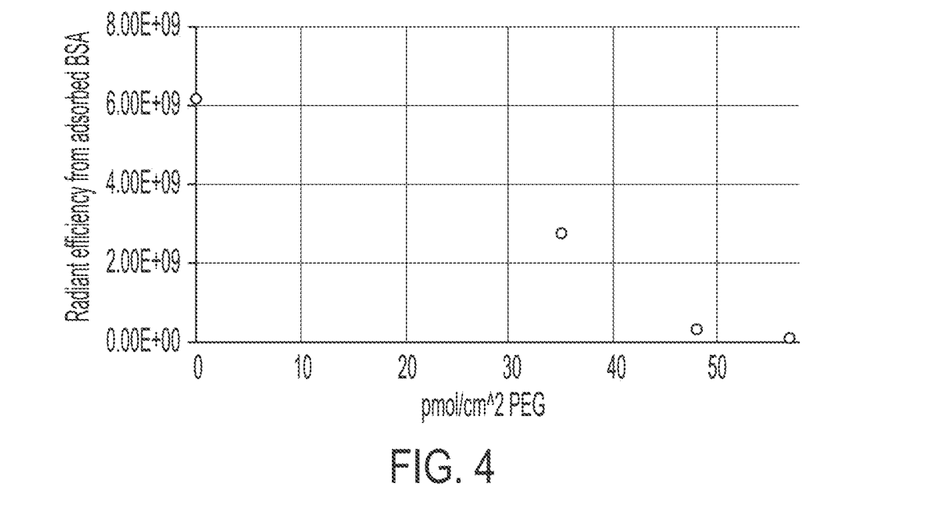
FIG. 4 is a graph shows the results in a fouling assay for particles having PEG densities of zero, 35, 48, and 58 pM/cm$^2$.

The carboxylic acids on the surface of a magnetic nanoparticle were converted to a reactive N-hydroxysuccinimide (NETS) attachment site using 1-ethyl-3-(3-dimethylaminopropyl)carbodiimide (EDC) and sulfonated N-hydroxysuccinimide (sulfo-NHS) in 25 millimolar (mM) 2-(N-morpholino)ethanesulfonic acid (MES) buffer having a pH of 4.6. The reaction was carried out with 167 microliters (μL) of magnetic nanoparticle solution (3% solids w/w) combined with 250 μL of 2% EDC by weight and 250 μL of 0.5% sulfo-NHS by weight. The reaction was allowed to proceed at room temperature for 30 minutes, then the particles were washed three times by magnetically concentrating the magnetic nanoparticles and replacing the buffer with 50% methanol at 4° C. The resulting NETS particles were resuspended in 500 μL of 50% methanol by weight in water containing 67.5 mM PEG, (e.g., amine-PEG5 k-methoxy). The methanol acted to condense the PEG by dehydrating the chains, causing the PEG to occupy a smaller volume and thus enabling attachment at higher density. The amine attachment site reacted with the NHS and resulted in PEG conjugated to the magnetic nanoparticle surface. The magnetic nanoparticles were then magnetically concentrated, washed with water three times, and they were redispersed in a storage buffer. The resulting level of PEG on the particle surface was determined using the barium chloride-iodide assay. For this assay, the magnetic particles were counted using nanoparticle tracking analysis (NTA), then are dissolved in concentrated hydrochloric acid (HCl) to lower their background absorbance. The assay was then carried out by adding 50 μL of the dissolved particles to 190 μL of a 0.5% barium chloride solution in water and adding 10 μL of 0.2 N iodide solution. The resulting absorbance at 535 nm was read after exactly 10 minutes and a standard curve was generated with known amounts of PEG. The results in terms of picomoles PEG per square centimeter ($pmol/cm^2$) for various PEGylation protocols are shown in FIG. 3. The 1-step method (FIG. 3) is the typical method suggested for commercial magnetic nanoparticles, in which EDC, sulfo-NHS, and PEG are added simultaneously to the carboxylated particles. The 2-step method is a modification of the original method, wherein the particles are first reacted with EDC and sulfo-NHS to produced NHS particles, and then the PEG-amine is added to the particles in a basic buffer. This substantially increases PEG density, but does not lead to sufficient surface PEG coverage to achieve the "brush" regime described above. As described herein, the 600 mM salt (60° C.) method at elevated temperatures relied on condensation of the hydrodynamic radius of PEG to achieve a smaller polymer footprint to enable higher coverage. For this method, NHS particles were produced using EDC and sulfo-NHS as usual, and then the particles were put in a 600 mM sodium sulfate solution and heated to 60° C. before the amine-PEG was added. However, even higher levels of PEG coverage were achieved with the use of cold methanol in the nucleophilic substitution step. This procedure resulted in a 10-fold increase in PEG density versus the standard 1-step procedure, and significant increase in PEG density over the modified 2-step procedure. A PEG passivation layer conjugated to magnetic nanoparticles using this method were stable on the surface for days, suggesting covalent linkage rather than nonspecific adsorption. This increased PEG density resulted in increased resistance to protein fouling on the magnetic nanoparticle surface. This was tested by incubating the magnetic nanoparticles having varying levels of PEG density with a serum protein (e.g., albumin). Magnetic nanoparticles with low and high PEG densities were incubated with fluorescein-conjugated bovine serum albumin (BSA), washed repeatedly, and then measured for the amount of BSA adsorbed to the surface via fluorescence. The results are shown in FIG. 4. As shown in FIG. 4, increasing PEG density clearly resulted in lower adsorption of BSA, one of the primary components of serum. At the highest PEG levels tested (e.g., greater than 50 $pmol/cm^2$), BSA adsorption was barely detectable. This is a strong advantage of increased PEG density, as adsorption of serum components (e.g., albumin) leads to rapid clearance in vivo and can interfere with specific binding by occluding targeting groups.

Figure 7:
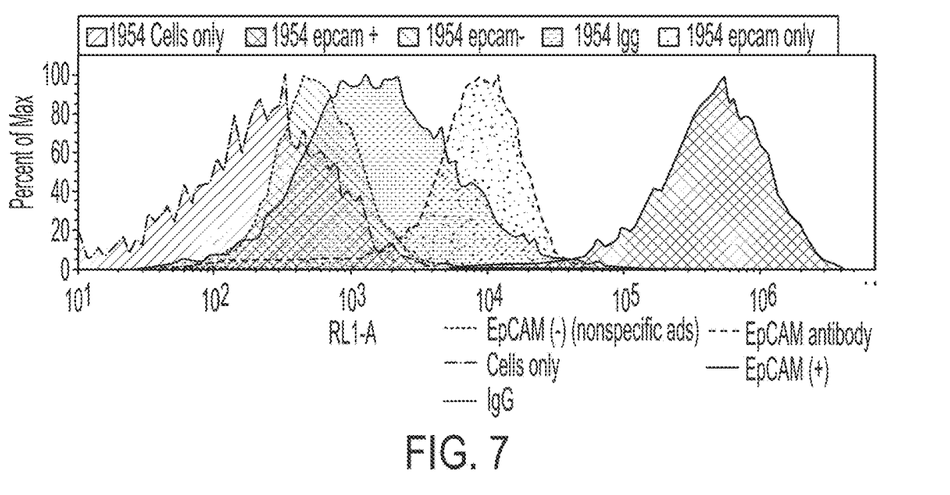
FIG. 7 is a graph showing Flow cytometry results for binding of anti-EpCAM targeted PEGylated nanoparticles to EpCAM-expressing cells.
Figure 8A:
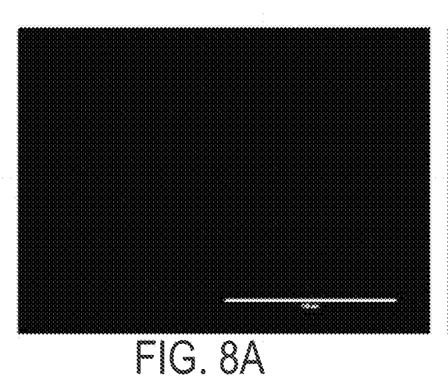
FIGS. 8A-8B show cell images of MDA-MB-436 cells (non EpCAM-expressing, FIG. 8A) and HCC1954 cells (EpCAM-expressing, FIG. 8B) after incubation with anti-EpCAM-conjugated magnetic particles.
Figure 8B:
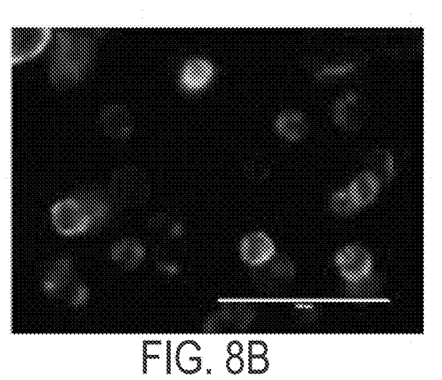
Figure 9:
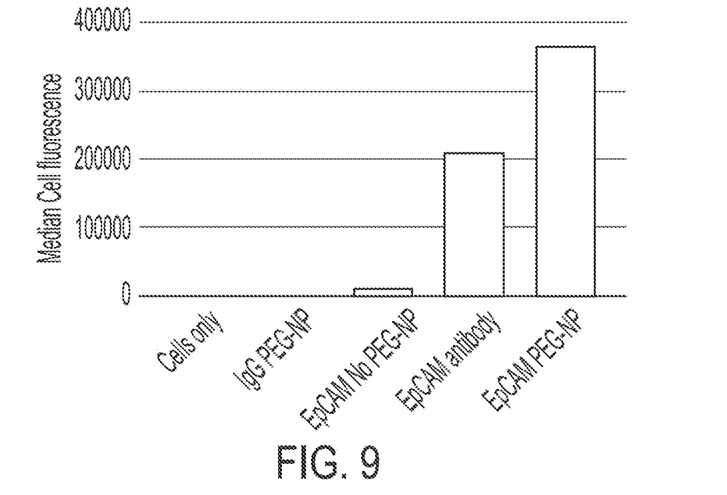
FIG. 9 is a graph showing median cell fluorescence of cell binding of EpCAM modified nanoparticles with HCC1954 (EpCAM+) cell line.

Example 10: Use of Functionalized Passivated Magnetic Nanoparticles Coated with EpCAM Antibody Passivated magnetic nanoparticles coated with anti-EpCAM antibodies were synthesized and examined for specific binding to EpCAM expressing cell lines. The antibodies were labeled with AlexaFluor 647 for tracking purposes. The targeted nanoparticles were incubated with EpCAM expressing (1954) and non-EpCAM expressing (436) cells and unbound nanoparticles were washed off by filtering the cells with a 5 μm plate (allowing the free particles, but not the cells, to pass through the plate). The cells were analyzed by flow cytometry (see FIG. 7), wherein the EpCAM expressing cells showed very high binding with anti-EpCAM nanoparticles, exceeding even the antibody on its own, and very little binding with non-targeted, IgG-conjugated nanoparticles. No binding was seen with non-EpCAM expressing cells. Non-PEGylated particles with anti-EpCAM antibody conjugated were also tested for cell binding, and were found to have significantly decreased specific binding to EpCAM-expressing cells as compared to the PEGylated, targeted particles. Cell images by fluorescence microscopy are shown in FIG. 8. FIG. 9 is a graph showing median cell fluorescence of cell binding of EpCAM modified nanoparticles with 1954 (EpCAM+) cell line. The highest degree of specificity was observed for the EpCAM-PEG-NP, which is over 10× more specific for 1954 cells than EpCAM-NP (no PEG).

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What we claim:

1. A functionalized magnetic nanoparticle, comprising:
   a. a magnetic nanoparticle;
   b. a poly(ethylene glycol) (PEG) passivation layer encapsulating the magnetic nanoparticle, wherein the PEG passivation layer comprises at least about 50 picomoles/cm$^2$ of PEG and wherein the PEG comprises at least one attachment site;
   c. a first chemical attachment moiety attached to the at least one attachment site of PEG; and
   d. a functional moiety, wherein the functional moiety comprises a second chemical attachment moiety attached to the first chemical attachment moiety.

2. The functionalized magnetic nanoparticle of claim 1, wherein the functional moiety is selected from the group consisting of a targeting agent, a therapeutic agent, an imaging agent, and any combination thereof.

3. The functionalized magnetic nanoparticle of claim 2, wherein the functional moiety is an antibody.

4. The functionalized magnetic nanoparticle of claim 1, wherein the functional moiety is labeled.

5. The functionalized magnetic nanoparticle of claim 1, wherein the first chemical attachment moiety is selected from the group consisting of Tetrazine (Tz), azide, biotin, pyridazine, hydrazine, hydroxylamine, carboxylic acid, thiol, and phosphine, and the second chemical attachment moiety is selected from the group consisting of Trans-Cyclooctene (TCO), alkyne, avidin or streptavidin, carbonyl, amine, maleimide, and azide.

6. The functionalized magnetic nanoparticle of claim 1, wherein the first chemical attachment moiety is selected from the group consisting of Trans-Cyclooctene (TCO), alkyne, avidin or streptavidin, carbonyl, amine, maleimide, and azide and the second chemical attachment moiety is selected from the group consisting of Tetrazine (Tz), azide, biotin, pyridazine, hydrazine, hydroxylamine, carboxylic acid, thiol, and phosphine.

7. A composition comprising a plurality of functionalized magnetic particles of claim 1.

8. A method of making a functionalized magnetic nanoparticle comprising
   a. providing a carboxylated magnetic nanoparticle;
   b. reacting the carboxylated magnetic nanoparticle with 1-ethyl-3-(3-dimethylaminopropyl)carbodiimide and sulfonated N-hydroxysuccinimide to provide N-hydroxysuccinimide coated magnetic nanoparticles; and
   c. covalently attaching poly(ethylene glycol) (PEG) to the N-hydroxysuccinimide coated magnetic nanoparticles in a surface activating solution under conditions that provide a PEG density of at least about 50 picomoles/cm$^2$.

9. The method of claim 8, wherein the PEG comprises at least one attachment site.

10. The method of claim 9, further comprising attaching a first chemical moiety to the at least one attachment site and attaching a second chemical moiety to the first chemical moiety, wherein the second chemical moiety is attached to a functional moiety.

11. The method of claim 8, wherein the surface activating solution comprises a high salt aqueous solution.

12. The method of claim 11, wherein the high salt aqueous solution comprises at least 400 μM sodium sulfate.

13. The method of claim 12, wherein the high salt aqueous solution comprises at least 600 μM sodium sulfate.

14. The method of claim 8, wherein the surface activating solution comprises an organic solvent.

15. The method of claim 12, wherein the high salt aqueous solution comprises a temperature of 20-80° C.

16. The method of claim 14, wherein the organic solvent comprises at least 50% methanol.

17. The method of claim 16, wherein the organic solvent comprises a temperature of 1-10° C.

18. A method of administering a functional moiety to a subject comprising administering to the subject one or more functionalized magnetic nanoparticles of claim 1.

* * * * *